(12) United States Patent
Delfort et al.

(10) Patent No.: US 8,870,982 B2
(45) Date of Patent: Oct. 28, 2014

(54) METHOD FOR CONVERTING BIOMASS INTO PRODUCTS CONTAINING ACETAL GROUPS AND USE THEREOF AS BIOFUELS

(75) Inventors: Bruno Delfort, Paris (FR); Remy Marchal, Chatou (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 930 days.

(21) Appl. No.: 12/678,512

(22) PCT Filed: Sep. 18, 2008

(86) PCT No.: PCT/FR2008/001309
§ 371 (c)(1),
(2), (4) Date: Jun. 26, 2010

(87) PCT Pub. No.: WO2009/071769
PCT Pub. Date: Jun. 11, 2009

(65) Prior Publication Data
US 2010/0263265 A1    Oct. 21, 2010

(30) Foreign Application Priority Data
Sep. 21, 2007  (FR) ..................... 07 06653

(51) Int. Cl.
*C10L 1/185* (2006.01)
*C07C 43/303* (2006.01)
*C10L 1/02* (2006.01)
*C07C 41/56* (2006.01)

(52) U.S. Cl.
CPC ............. *C07C 41/56* (2013.01); *Y02E 50/13* (2013.01); *C10G 2300/1014* (2013.01); *C10L 1/026* (2013.01)
USPC .......................................... 44/444; 568/594

(58) Field of Classification Search
CPC ...... C07C 41/56; C07C 43/303; C07C 29/86; C07C 51/43; C10G 2300/1014; C10G 2300/1011; Y02E 50/13; C11B 3/005; C11B 3/02; C11B 13/00; C10L 1/185; C10L 1/026; C10L 1/04; C10L 1/06; C10L 1/08; C10L 1/1824; C10L 1/1857; C10L 1/182; C10L 1/02; C10L 1/18; C10L 10/02; C10L 10/14; C10L 1/14; C10L 1/1616; C10L 1/1826; C10L 1/1852; C10L 1/1881; C10L 1/19; C02F 1/26; C11C 3/003; C11C 3/00
USPC ........... 44/438, 308, 444, 594, 446, 453, 307; 554/174, 124, 167, 168, 169, 170
See application file for complete search history.

(56) References Cited

U.S. PATENT DOCUMENTS

2007/0260078 A1*  11/2007  Bhat et al. .................. 554/174
2010/0186289 A1*   7/2010  Bradin et al. ................ 44/308
2010/0263264 A1*  10/2010  Augier et al. ................ 44/438

FOREIGN PATENT DOCUMENTS

| FR | 2 497 223 A1 | | 7/1982 |
| FR | 2 544 738 A1 | | 10/1984 |
| FR | 0704673 | * | 6/2007 |
| WO | WO 00/17290 A1 | | 3/2000 |
| WO | WO 2005/010131 A1 | | 2/2005 |

OTHER PUBLICATIONS

International Search Report of PCT/FR2008/001309 (Jun. 17, 2009).
F. Frusteri et al., "Oxygenated Additives Production for Diesel Engine Emission Improvement", Chemical Engineering Journal, vol. 134, No. 1-3 (2007) pp. 239-245.

* cited by examiner

*Primary Examiner* — James Goloboy
*Assistant Examiner* — Chantel Graham
(74) *Attorney, Agent, or Firm* — Millen, White, Zelano, Branigan, P.C.

(57) ABSTRACT

The invention describes a method of converting biomass to products that can be incorporated into the diesel fuel pool, comprising a first stage of fermentation of renewable raw materials of vegetable origin at the end of which a least one alcohol and at least one compound containing a carbonyl group are obtained, and a second stage corresponding to an acetalization reaction involving said alcohol and said compound containing a carbonyl group.

11 Claims, No Drawings

METHOD FOR CONVERTING BIOMASS INTO PRODUCTS CONTAINING ACETAL GROUPS AND USE THEREOF AS BIOFUELS

FIELD OF THE INVENTION

The present invention comes within the scope of the current development of biorefineries. It relates to a method of converting biomass to products containing acetal groups and their use in the diesel fuel pool.

The present invention thus consists in the fermentation of renewable raw materials of vegetable origin, followed by their conversion to products that are substitutes of products nowadays predominantly obtained from the conversion of raw materials of fossil origin such as fuels or products manufactured by the chemical industry.

More precisely, the invention consists in converting products resulting from various fermentation types to a chemical species of the acetal family, which will thereafter be advantageously used as biofuels) or incorporated into fuels or biofuels or compositions containing same.

BACKGROUND OF THE INVENTION

The biorefinery is a key element for an integrated bioresources management. During the Rio de Janeiro congress in June 1992, 170 states have integrated the principle of integrated management into their action programme for the twenty-first century: in September 2002, this principle has even been reasserted during the world summit in Johannesburg. According to the US Department of Energy's definition, the biorefinery is a global plant concept wherein the biomass resource is extracted, then converted to a wide range of upgradable products. The biorefinery logical scheme is borrowed from petrochemistry. The intermediate compounds (sometimes referred to as synthons) derived from sugars occupy a central position since they lead to the final products that will be launched onto the market (Ohara et al., *Appl. Microbiol. Biotechnol.* 62, 474-477 (2003); Kamm and Kamm, *Appl. Microbiol. Biotechnol.* 62, 137-145 (2004)). Alcohols and ketones belong to these important synthons obtained from the biomass.

In a biorefinery, the streams of alcohols and of compounds containing a carbonyl group such as mainly acetone can result from the distillation of the fermentation musts or their separation by means of membranes.

Examples of the various fermentation types known to the person skilled in the art and using renewable raw materials of vegetable origin are:
  acetonobutylic or ABE (acetone-butanol-ethanol) fermentation mainly using the *Clostridium acetobutylicum* bacterial species. ABE fermentation produces two main families of compounds, alcohols (ethanol, butanol) on the one hand and a carbonyl-containing compound, acetone, on the other hand (Spivey M. J. (1978): The acetone/butanol/ethanol fermentation. Process Biochem. 13:2-25). In end-of-culture musts, the alcohols are commonly obtained at a concentration ranging between 150 and 190 mM, whereas the final acetone concentration ranges between 85 and 170 mM;
  IBE (isopropanol-butanol-ethanol) fermentation that mainly involves the *Clostridium bejerinckii* strains, formerly classified as *Clostridium butylicum*. IBE fermentation produces three main alcohols (ethanol, butanol and isopropanol), as well as acetone. The final alcohol concentrations of IBE fermentation are close to those of the ABE fermentation. However, the acetone concentration is generally lower than in the ABE fermentation;
  ethanolic fermentation. In a biorefinery, the ethanol is generally obtained from the alcoholic fermentation carried out with the *Saccharomyces cerevisiae* yeast. It is however possible to use other micro-organisms, notably the *Zymomonas mobilis* bacterium. With *Saccharomyces cerevisiae* and the species of *Saccharomyces* gender, the final ethanol content is close to a hundred grams per liter of medium.

The substrates of the ABE and IBE fermentations are either simple sugars, monomers or dimers such as glucose and saccharose, respectively, or complex sugars such as starch. The main amylaceous raw materials are cereals (wheat, corn, barley) and potatoes. From amylaceous materials, the monomeric sugars can be obtained by hydrolysis with commercial amylases. However, many *Clostridium acetobutylicum* and *Clostridium bejerinckii* strains are capable of using starch directly. With these strains, prior hydrolysis of the starch is thus not necessary. In a similar way to amylaceous substrates, the lignocellulosic substrates can be hydrolyzed by commercial hydrolases (cellulases) in order to give C6 (mainly glucose) and C5 (xylose and arabinose) monomeric sugars. *Clostridium acetobutylicum* and *Clostridium bejerinckii* can use C5 as well as C6 monomeric sugars.

Conventionally, the fermentation products are sent to the gasoline pool. In fact, the ABE mixture has a high octane number and, in admixture with gasoline, it causes no stability problems in the presence of water traces or demixing phenomena. Its cetane number is too low to be advantageously incorporated into the diesel fuel pool.

It has been discovered that, by cleverly combining the various streams from the aforementioned fermentation units, according to a chemical acetalization reaction involving at least one alcohol with at least one compound containing a carbonyl group such as ketones, and more precisely acetone, according to the general scheme illustrated below, it is possible to obtain an acetal or a mixture of acetals compatible and soluble with diesel fuels or biofuels and usable in Diesel engines.

SUMMARY OF THE INVENTION

The invention describes a method of converting biomass to products that can be incorporated into the diesel fuel pool, comprising a first stage (a) of fermentation of renewable raw materials of vegetable origin at the end of which a least one alcohol and at least one compound containing a carbonyl group are obtained, and a second stage (b) corresponding to an acetalization reaction involving said alcohol and said compound containing a carbonyl group obtained in stage (a).

The method according to the invention thus comprises a third stage (c) wherein the mixture from stage (b) is incorporated into a diesel fuel base and/or a biodiesel fuel.

DETAILED DESCRIPTION

The method according to the present invention affords the advantage of using feeds coming from renewable raw materials of vegetable origin within the context of a biorefinery. All the reactants necessary for the acetalization reaction and the production of acetals compatible with the fuels are directly obtained during the first stage of fermentation of the biomass-based products. All of the coproducts from the fermentation are thus used to carry out the acetalization reaction.

The products obtained by means of the method according to the present invention can be used as fuels or incorporated into a fuel base. If is thus possible to send products directly coming from the biomass to the diesel fuel pool.

The raw materials of vegetable origin are subjected to a first fermentation stage. These raw materials can come from sugar plants (beet, sugar cane), amylaceous plants (corn, wheat, barley, potato) or lignocellulose (agricultural residues, forest residues, short-rotation coppice).

The raw materials can be subjected, prior to stage (a), to a pretreatment and/or hydrolysis, these stages being sometimes necessary to extract the C5 and C6 fermentiscible sugars. For the lignocellulosic raw materials, hydrolysis is usually preceded by a treatment that makes the cellulose and the hemicelluloses accessible to hydrolases. The main treatments before hydrolysis are alkaline pretreatments (with soda, for example, as used in the paper-making industry), acid pretreatments (sulfuric acid between 1% and 3%) with variable durations and temperatures, and stream pretreatments also referred to as flash hydrolysis or steam explosion. In the steam pretreatment, an autohydrolysis occurs under the effect of the acetyl groups released from the many substituted sugars of the hemicelluloses, thus operating in situ partial hydrolysis of these polymers. Steam pretreatment also leads to fusion of the lignins, followed by their recondensation as droplets upon cooling, and intense destructuration of the material upon explosive release of the product. These combined three effects contribute towards a very noticeable increase in the enzymatic susceptibility of the steam pretreated vegetable. A fourth pretreatment type is pretreatment with solvents such as hot ethanol.

The raw materials of vegetable origin are then subjected to the fermentation stage proper, which can be of three types:

ABE fermentation, and/or

IBE fermentation, and possibly ethanolic fermentation.

ABE or IBE fermentations are in fact essential in the method according to the present invention because they allow to obtain the products necessary for the acetalization reaction. They are possibly complemented by an ethanolic type fermentation, thus allowing a larger stream of alcohol(s) to be obtained.

After this fermentation stage, various alcohol streams are collected depending on the type of fermentation that has occurred, as well as streams of compounds containing a carbonyl group. In the case of ABE and IBE fermentations, small amounts of carboxylic acids (acetic and butyric) and gases (hydrogen and $CO_2$) are also obtained.

These various streams (alcohols and compounds containing a carbonyl group) can result from the distillation of the fermentation musts or from their separation through membranes.

The alcohols obtained are essentially ethanol, n-butanol or isopropanol. The compound containing a carbonyl group is mainly acetone from ABE and/or IBE fermentation.

These various streams are mixed together and they make up the reactants necessary for the reaction leading to the formation of at least one acetal.

In fact, the general acetal synthesis reaction can be written as follows:

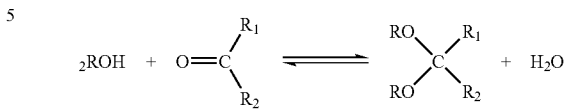

where ROH represents an alcohol mainly selected from among ethanol, isopropanol, n-butanol . . . and where $R_1$ and $R_2$ represent hydrogen atoms or alkyl radicals such as methyl groups. When $R_1=R_2=CH_3$, the carbonyl-containing compound is acetone and the reaction can be written as follows:

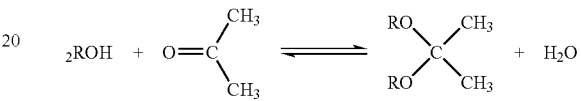

When a mixture of several alcohols is used, the reaction becomes, for example in the case of a mixture of two alcohols:

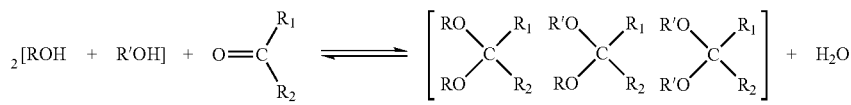

wherein ROH and R'OH represent each an alcohol mainly selected from among ethanol, isopropanol, n-butanol . . . .

When $R_1=R_2=CH_3$, the carbonyl-containing compound is acetone and the reaction can be written as follows:

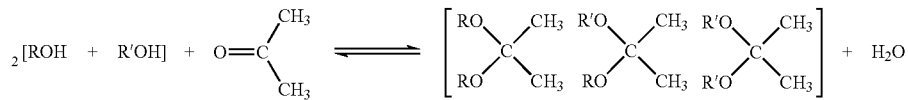

The number of different alcohols and of different carbonyl-containing compounds involved in the acetalization reaction is not limitative.

Examples of acetals thus formed according to the invention are 2,2-diethoxy propane, diisopropoxy-2,2-propane, di-n-butoxy-2,2-propane, ethoxy-2-isopropoxy-2-propane, ethoxy-2-n-butoxy-2-propane, n-butoxy-2-isopropoxy-2-propane.

This general acetal formation reaction is a well-known reaction in organic chemistry. It is a balanced reaction involving 2 moles of alcohol to 1 mole of ketone or aldehyde. The reaction produces an acetal molecule and a water molecule. It is a balanced reaction that can be promoted using an excess amount of one of the reactants or by removing the condensation water during the reaction.

In order to shift the equilibrium in the direction favourable to acetal formation, excess alcohol in relation to stoichiometry is generally used. The molar ratio of the number of moles of alcohol(s) to that of ketone or aldehyde ranges between 2.1 and 20, preferably between 2.2 and 6. The reaction can also be promoted by removing the condensation water formed during the reaction. It is therefore possible to operate for example in the presence of a molecular sieve.

These two principles are sometimes applied simultaneously.

The reaction temperature ranges between the ambient temperature and 180° C. More generally, when using acetone, the reaction is carried out at 56° C., which corresponds to the boiling temperature of acetone at atmospheric pressure. It is also possible to operate at a higher temperature and at a higher pressure than the atmospheric pressure using an autoclave type equipment allowing to work under pressure.

The reaction of acetal formation from alcohols and ketones or aldehydes is generally catalyzed by the acids whose concentration can range between 0.1 and 5% by mole in relation to the number of moles of compounds containing a carbonyl group, preferably between 0.3 and 1.5% by mole.

Non-exhaustive examples of the most commonly used catalysts are sulfuric acid, hydrochloric acid, paratoluenesulfonic acid and heterogeneous type acid catalysts like sulfonic resins such as, for example, some Amberlyst™ resins, notably Amberlyst 15.

The reaction mechanism is a cationic mechanism presented in detail hereafter.

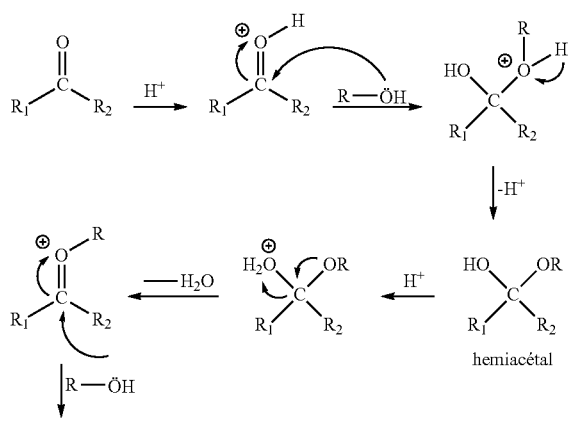

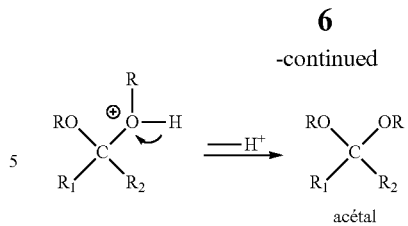

Addition of a first molecule of alcohol on a carbonyl function leads to the formation of a hemiacetal. The formation of a hemiacetal is reversible and the intermediate of this reaction is an oxonium ion. The reaction starts with the protonation of the carbonyl oxygen, followed by the loss of a molecule of water. Most hemiacetals are unstable in relation to the carbonyl-containing compounds they come from (on the other hand, the hemiacetals that form through intramolecular cyclization are often stable if the cycle formed comprises five or six atoms). In an acid medium, hemiacetals can undergo protonation followed by a water elimination reaction that leads to an unstable non-protoned oxonium ion, very reactive to a second alcohol molecule, which leads after the loss of a proton to the formation of an acetal. In fact, each acetal formation stage is reversible.

Acetals can also be prepared by reaction between an alcohol and an already existing acetal. It is an alcohol exchange reaction from an acetal, referred to as transacetaiization. This acid-catalyzed reaction is reversible. It is promoted by the continuous elimination of the leaving alcohol.

Acetal or acetal mixtures preparation can be achieved batchwise in a stirred reactor or on a continuous basis in a piston or tubular type reactor comprising a heterogeneous solid catalyst. The acetalization reaction is followed by a separation stage allowing the water and the excess reactants to be removed.

A mixture of acetals is thus obtained, which can be directly sent to the fuel pool of the biorefinery.

The method according to the invention as a whole can be summed up by means of the following flowsheet:

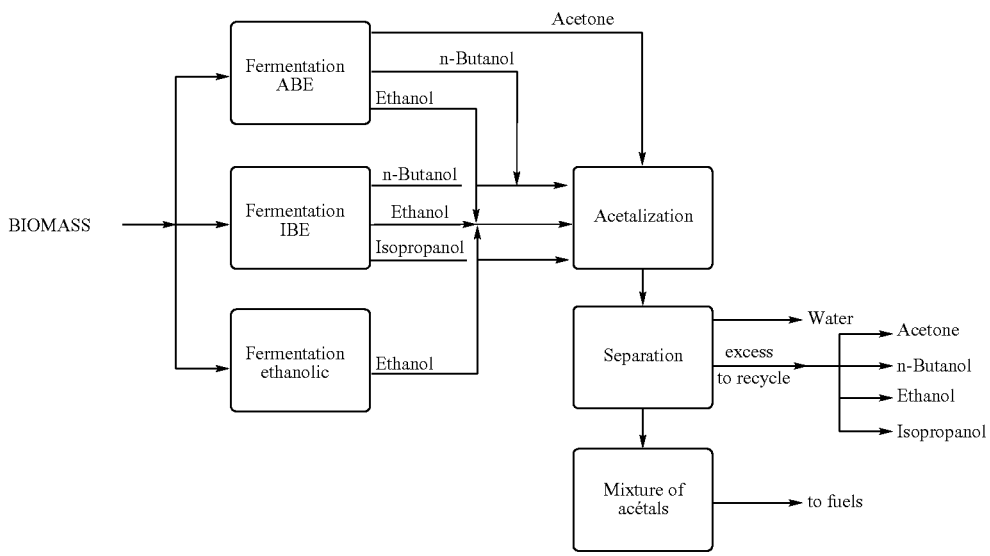

It is also possible to complement the acetone stream resulting from the various fermentations with another outer source of carbonyl-containing compounds.

EXAMPLES

Example 1

Production of Acetone, Butanol and Ethanol from Lignocellulosic Substrates

The substrate used is corn cob. The cob (5.5 tons) is steam pretreated on a continuous basis in a STAKE machine at a pressure of 13 to 14 bars for 3 minutes. The pretreated biomass divided into two equivalent batches is subjected to enzymatic hydrolysis in a 25-m³ reactor for 24 hours with cellulases of *Trichoderma reseii* CL 847, at a rate of 30 FPU (filter paper unit) per gram of dry matter. At the end of the operation and after combining the two hydrolysate batches, the suspended insoluble materials are eliminated by centrifugation and 50 m³ of a clarified hydrolysate whose sugar composition is as follows: glucose 41.5 g/l, xylose 23 g/l and arabinose 1 g/l are obtained.

The sugar hydrolysate is supplemented with 0.5 g/l $KH_2PO_4$, 0.2 g/l $MgSO_4$, $7H_2O$, 10 mg $FeSO_4$, $7H_2O$ and 3 g/l yeast extract. It is seeded with a preculture of the *Clostridium acetobutylicum* NCIB 2951 strain at a seeding rate of 5% (v/v) under rigorous aseptic conditions obtained after sterilizing the hydrolysate at 110° C. for 40 min. During the acidogen growth phase, the pH value is set at 5.5 by addition of ammonia water. After 50-hour culture, a final must comprising 7.8 g/l acetone, 12.4 g/l butanol and 0.3 g/l ethanol is obtained, the released gases representing 31 l/l of the culture medium. The fermentation must is sent to distillation after being heated to 97° C. In this first separation stage, the butanol, the acetone and 90% ethanol are steam entrained. The condensate contains approximately 50% (v/v) water and 50% solvents. It is sent to ABE distillation where ethanol plus acetone is separated from water plus butanol. The "acetone-ethanol" distillation then separates these two products. The ABE distillation residue is decanted to obtain separation of the butanol and of the water. At the end of this process, 362 l acetone, 575 l butanol and 12 l ethanol are obtained.

Example 2

Production of Ethanol from Lignocellulosic Substrates

The cob hydrolysate as obtained in Example 1 is supplemented with $KH_2PO_4$ (3 g/l), $(NH_4)_2SO_4$ (2 g/l), $MgSO_4$, $7H_2O$ (0.5 g/l), yeast extract (1 g/l). It is fermented with the *Saccharomyces cerevisae* ATCC 2062 yeast. After 12-hour culture at a temperature of 28° C. at the initial pH value of 4.5, a final must containing 20 g/l ethanol that is recovered by distillation is obtained.

Example 3

Synthesis of di-n-butoxy-2.2-propane from the Products Obtained in Example 1

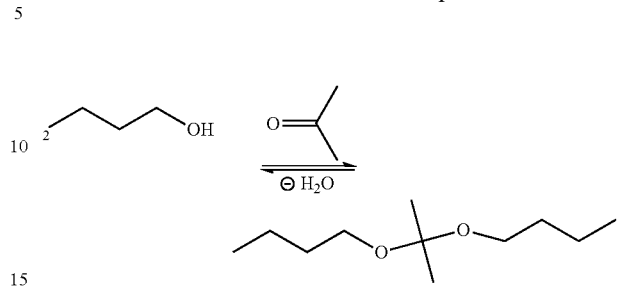

The whole amount of the n-butanol prepared in Example 1, i.e. 575 liters or approximately 465.7 kg (6294 moles), are fed into a reactor equipped with a stirring system, a reflux column and a temperature control system including a water cooling coil system. 115 liters, i.e. approximately 91 kg (1573 moles) of acetone taken from the acetone collected in Example 1, as well as 3 kg Amberlyst 15 sulfonic resin, i.e. approximately 14 molar equivalents of acid function, are then introduced. The medium is kept under agitation for one hour while controlling the temperature in order to remain at ambient temperature, then the medium is brought to reflux for 6 hours. After returning to ambient temperature, the reactor is emptied by gravitation through a filter so as to leave the solid catalyst in the reactor where it can be used again for the next operation. The mixture obtained is then sent to a distillation column where separation of the residual acetone, the excess n-butanol and the condensation water is carried out under conventional conditions known to the person skilled in the art. 271 kg of a liquid corresponding to di-n-butoxy-2.2-propane are recovered.

Example 4

Synthesis of an Acetal Mixture from the Products Obtained in Examples 1 and 2

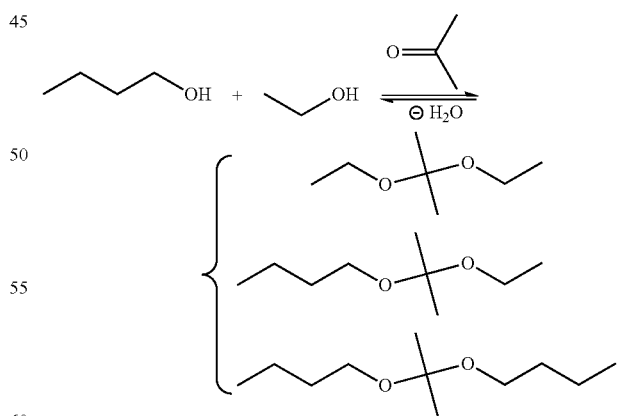

The whole amount of the acetone prepared in Example 1, i.e. 362 liters or approximately 286 kg (4937 moles), are fed into a reactor equipped with a stirring system, a reflux column and a temperature control system including a water cooling coil system. All of the n-butanol prepared in Example 1, i.e. 575 liters or approximately 465.7 kg (6294 moles), as well as all of the ethanol prepared in Example 1, i.e. 12 liters or approximately 15.2 kg (300 moles), are then introduced. 350 liters or approximately 276 kg (6000 moles) of ethanol prepared from lignocellulosic substrates under the conditions described in Example 2 are added to this medium. 8.5 kg Amberlyst 15 sulfonic resin, i.e. approximately 41.6 molar equivalents of acid function, are then added. The medium is kept under agitation for two hours while controlling the temperature in order to remain at ambient temperature, then the medium is brought to reflux for 7 hours. After returning to ambient temperature, the reactor is emptied by gravitation through a filter so as to leave the solid catalyst in the reactor where it can be used again for the next operation. The mixture obtained is then sent to a distillation column where separation of the residual acetone, the excess ethanol, the excess n-butanol and the condensation water is carried out under conventional conditions known to the person skilled in the art. 761 kg of a liquid acetal mixture whose molar composition is 21% diethoxy-2.2-propane, 53% ethoxy-2-n-butoxy-2-propane and 26% di-n-butoxy-2.2-propane are recovered.

Example 5

Mixtures of a diesel fuel of density 0.832 at 15° C., with a sulfur content of 30 ppm and a cetane number of the order of 53 with respectively 5%, 10% and 30% by volume of the acetal mixture as prepared in Example 4 are achieved. The products are miscible. The cetane numbers of the mixtures measured according to the EN ISO 5165 method are 53, 53 and 54 respectively, which confirms the compatibility of the acetals prepared with diesel fuels.

Example 6

A mixture of a diesel fuel of density 0.832 at 15° C., with a sulfur content of 30 ppm and a cetane number of the order of 53, comprising 5% by volume of a rapeseed oil methyl ester commonly referred to as biodiesel meeting the EN 14414 European standard, and 5% by volume of the acetal mixture as prepared in Example 4 is achieved. The products are miscible. The cetane number of the mixture measured according to the EN ISO 5165 method is 53, which confirms the compatibility of the acetals prepared with diesel fuel and biodiesel fuel compositions.

Example 7

A mixture of a rapeseed oil methyl ester commonly referred to as biodiesel, satisfying the EN 14414 European standard and of 10% of the acetal mixture as prepared in Example 4 is achieved. The products are miscible. The cetane number of the mixture measured according to the EN ISO 5165 method is 51, which confirms the compatibility of the acetals prepared with biodiesel fuel.

The invention claimed is:

1. A method of converting alcohol compounds and carbonyl containing compounds resulting from biomass fermentation to acetal family products, comprising
   a first stage (a) of fermentation of acetonobutylic (or ABE (acetone-butanol-ethanol)) and/or IBE (isopropanol-butanol-ethanol) type of renewable raw materials of vegetable origin, whereby a least one alcohol and at least one compound containing a carbonyl group are produced, and
   a second stage (b) of acetalization to produce an acetal or a mixture of acetal products from the at least one alcohol and at least one compound containing a carbonyl group obtained in stage (a), whereby the alcohol and the carbonyl compounds in the product are produced directly from ABE and/or IBE and ethanolic fermentations.

2. The method as claimed in claim 1, wherein the raw materials of vegetable origin come from sugar plants, amylaceous plants or lignocellulosic plants.

3. The method as claimed in claim 1, wherein the raw materials are subjected to a pretreatment and/or hydrolysis prior to stage (a).

4. The method as claimed in claim 1, wherein the acetalization reaction of stage (b) is catalyzed by acids whose concentration ranges between 0.1% and 5% by mole in relation to the number of moles of compound comprising a carbonyl group.

5. The method as claimed in claim 4, wherein the catalyst is selected from among sulfuric acid, hydrochloric acid, para-toluenesulfonic acid or acid catalysts of heterogeneous type such as sulfonic resins.

6. The method as claimed in claim 1, wherein stage (b) is carried out at a temperature ranging between ambient temperature and 180° C.

7. The method as claimed in claim 1, wherein stage (b) is carried out batchwise in a stirred reactor.

8. The method as claimed in claim 1, wherein stage (b) is carried out on a continuous basis in a piston or tubular type reactor.

9. The method as claimed in claim 1, comprising a stage (c) wherein the mixture from stage (b) is incorporated into a diesel fuel base and/or a biodiesel fuel.

10. The method as claimed in claim 2, wherein the raw materials are subjected to a pretreatment and/or hydrolysis prior to stage (a).

11. A method of converting alcohol compounds and carbonyl-containing compounds resulting from biomass fermentation to acetal family products, comprising
   (a) fermentation of biomass of vegetable origin by ethanolic, acetonobutylic (or ABE (acetone-butanol-ethanol)) and/or IBE (isopropanol-butanol-ethanol) fermentation reactions, whereby a least one alcohol and at least one compound containing a carbonyl group are produced, and
   (b) acetalization of the at least one alcohol and at least one compound containing a carbonyl group obtained in step (a) to produce an acetal or a mixture of acetal products,
   whereby the alcohol and the carbonyl compounds in the product are produced directly from ABE and/or IBE and ethanolic fermentations.

* * * * *